United States Patent [19]

Duplyakin et al.

[11] Patent Number: 5,925,801
[45] Date of Patent: Jul. 20, 1999

[54] PROCESS FOR PREPARING HIGH-OCTANE GASOLINE COMPONENTS, AND A CATALYST

[75] Inventors: Valery Kuzmich Duplyakin; Valentina Petrovna Finevich; Gleb Alexandrovich Urzhuntsev; Alexandr Ivanovich Lugovskoi, all of Omsk, Russian Federation

[73] Assignee: Institut Kataliza Imeni G.K. Boreskova Sibirskogo Otdelenia Rossiiskoi Akademii Nauk, Lavrentieva, Russian Federation

[21] Appl. No.: 08/776,893

[22] PCT Filed: Aug. 11, 1995

[86] PCT No.: PCT/RU95/00174

§ 371 Date: Feb. 13, 1997

§ 102(e) Date: Feb. 13, 1997

[87] PCT Pub. No.: WO96/05155

PCT Pub. Date: Feb. 22, 1996

[30] Foreign Application Priority Data

Aug. 15, 1994 [RU] Russian Federation ............. 94029836

[51] Int. Cl.$^6$ ............... C07C 2/58; B01J 27/14; B01J 27/053
[52] U.S. Cl. .......... 585/721; 585/709; 585/730; 585/731; 585/732; 502/208; 502/216; 502/217; 502/224; 502/226; 502/227; 502/231
[58] Field of Search .................. 585/709, 721, 585/730, 731, 732; 502/208, 216, 217, 224, 226, 227, 231

[56] References Cited

U.S. PATENT DOCUMENTS

| | | | |
|---|---|---|---|
| 2,804,491 | 8/1957 | May et al. | 260/683.4 |
| 3,251,902 | 5/1966 | Garwood et al. | 260/683.64 |
| 3,549,557 | 12/1970 | Bolton et al. | 252/455 |
| 3,655,813 | 4/1972 | Kirsch et al. | 260/683.43 |
| 3,855,342 | 12/1974 | Huang et al. | 260/683.44 |
| 3,862,258 | 1/1975 | Huang et al. | 260/683.44 |
| 3,893,942 | 7/1975 | Yang | 252/411 |
| 4,377,721 | 3/1983 | Chester et al. | 585/722 |
| 4,384,161 | 5/1983 | Huang | 585/722 |
| 4,956,518 | 9/1990 | Child et al. | 585/726 |
| 4,992,615 | 2/1991 | Huss, Jr. et al. | 585/722 |
| 4,992,616 | 2/1991 | Chou et al. | 585/722 |
| 5,191,147 | 3/1993 | Degnan et al. | 585/722 |
| 5,276,242 | 1/1994 | Wu | 585/709 |
| 5,365,009 | 11/1994 | Uppal et al. | 585/722 |

FOREIGN PATENT DOCUMENTS

| | | | |
|---|---|---|---|
| 542620 | 5/1993 | European Pat. Off. | |
| 0561284 | 9/1993 | European Pat. Off. | C07C 2/58 |
| 2631956 | 12/1989 | France | C07C 2/58 |
| 1242641 | 4/1985 | Japan | B01J 27/02 |

OTHER PUBLICATIONS

Chemical Abstract 106:216817b "Solid acid catalysts for isobutane alkylation" Oct. 2, 1986 (corresponds JP 61 242641).
Chemical Abstract 94:215268v "Solid acid catalyst for hydrocarbon isomerization and alkylation" Apr. 3, 1981 (Corresponds JP 59 40056).
Chemical Abstract 124696u "Lsoparaffin–olefin alkylation with added water and with a complex of a macroreticular acid cation exchange resin and boron trifluoride" Jan. 21, 1975 (corresponds US 3,862,258).
Chemical Abstract 94:215267u "Solid acid catalyst for hydrocarbon isomerization and alkylation" Apr. 3, 1981 (corresponds JP 59 6181).
Chemical Abstract 85:32398g "Catalyst for alkylation of paraffinic or aromatic compounds" Apr. 22, 1976 (corresponds JP 51 63386).
Abstract, U.S. Patent 3,855,342.
Abstract, U.S. Patent 3,862,258.
Abstract, U.S. Patent 4,377,721.
Abstract, U.S. Patent 4,384,161.
Abstract, U.S. Patent 4,992,616.
Abstract, EP Patent Publication 433954.
Abstract, JP 61 242641 of Oct. 28, 1986.

Primary Examiner—Glenn A. Caldarola
Assistant Examiner—In Suk Bullock
Attorney, Agent, or Firm—Ladas & Parry

[57] ABSTRACT

A process for preparing high-octane gasoline components consists in that a feed stock, composed of isobutane and olefins, preferably butylenes, in a molar ratio between 1 and 40, is contacted at temperatures of from about 50 to about 160° C. and at pressures of from about 1 to about 40 atm. with a heterogeneous acid catalyst, whose active component is a metal-complex or metaloxopolymeric compound of the general formula $H_k(Me^1)$; $(Me^2)_m O_n X_p$ wherein k=1–6; j=1–3; m=1–5; n=1–10, p=2–10, dispersed in a porous organic or inorganic matrix, followed by the extraction regeneration of the deactivated catalyst with an organic or inorganic solvent.

17 Claims, No Drawings

PROCESS FOR PREPARING HIGH-OCTANE GASOLINE COMPONENTS, AND A CATALYST

TECHNICAL FIELD

The present invention relates to catalytic chemistry, more particularly, to processes for preparing high-octane gasoline components in the oil refining and petrochemical industries.

The present invention relates to an alkylation process which is based on reaction of isoparaffins with olefins to form isoparaffin hydrocarbons having a higher molecular weight.

PRIOR ART

Alkylation of isobutane with butylenes is traditionally used in industry to form a mixture of isoparaffin hydrocarbons, a so-called alkylate with an octane number of from 82 to 92 MM. Typical catalysts of industrial alkylation processes are sulfuric acid or fluorinated derivatives thereof (EP 0 433 954 A1) and hydrofluoric acid. Artificial cold is used a process involving sulfuric acid to maintain low reaction temperatures at 3 to 8° C., at acid concentrations from about 88 to about 94% by weight by continuously adding a fresh acid to the reaction system and removing the spent one.

Hydrofluoric and sulfuric acid alkylation plants are being used in the world. However, hydrofluoric acid is more dangerous than sulfuric acid, that is why some countries refuse the construction of plants using this catalyst. A choice between these processes depends on an amount of operating costs and/or safety in operations.

A hydrofluoric acid alkylation process usually uses 0.5 to 0.8 kg of acid per ton of alkylate, whereas a sulfuric acid alkylation process uses a much greater amount of acid, namely 60–100 kg per ton of alkylate.

High acid consumption necessitates the use of acid regeneration plants which should be used in combination with an alkylation plant.

The world annual production of alkylate amounts to 51 mln. tons and is expected to grow by 5 times before the year of 2000 due to more rigid ecological norms for motor gasoline with respect to the content of tetraethyl lead, benzene and a total amount of aromatic hydrocarbons.

The widely known industrial alkylation technologies are disadvantageous in:

high toxicity and corrosive aggression of sulfuric and hydrofluoric acids, problems of utilization of the spent acid, necessity for recovering a catalyst from a product mixture and subsequently making it alkaline, these factors cause a high ecological danger and insufficient economic efficiency from the industrial point of view.

In solving these problems, the last decade has witnessed intensive investigations on developing solid acid catalysts and carrying out an alkylating process in a gas (raw material)—solid (catalyst) or liquid (raw material)—solid (catalyst) heterogeneous system. This makes the process ecologically safer.

It is advisable to single out several approaches to the development of solid alkylation catalysts.

The first approach suggests improving an alkylation catalyst by applying (heterogenizing) an (traditional) active component that has been known for a long time to inorganic supports. The peculiar feature of this approach is using, as active components, both proton-containing acids ($H_2SO_4$; HF; $CF_3SO_3H$) and Lewis acids ($AlCl_3$, $BF_3$, $BCl_3$, $SbF_5$, and the like). The nature of patented supports is much more variegated. Two large groups of supports may be singled out.

1. Non-zeolite ones represented by oxides or a mixture of Group III or IV metal oxides modified with the additives of elements of from Groups I to VIII, more often than not with the oxides of rare-earth elements.

2. Wide-pore zeolites of X, Y, ZSM, or Beta, etc. types. This approach is illustrated by a number of the patented catalytic systems and processes based thereon.

In U.S. Pat. No. 2,804,491 the catalyst is represented by an alumina gel stabilized with silica and containing boron trifluoride. Solid inorganic Group IV metal oxides modified with sulfuric acid, represent the subjects of the inventions in Japanese Patents No. 51-63386; No. 57-3650; No. 59-40056, No. 59-6181 and also in U.S. Pat. No. No. 3,251,902; No. 3,655,813; No. 4,377,721 for a process for alkylating isoparaffin hydrocarbons with olefins.

Sulfuric or fluorosulfonic acid applied to an inorganic support is claimed as alkylation catalysts in EP No: 433 954 A1.

Both acids applied in the form of a liquid phase to an inorganic or an organic support belonging to classes formed by macroseticular polymers, zeolites, oxides of Groups III–VIII metals or a combination thereof are claimed as catalysts for the alkylation of isoparaffins with olefins in European Application No. 0 542 620 A1.

Lewis acids of $AlCl_3$, $BF_3$, $BCl_3$, $SbF_5$ types, applied to solid non-zeolite inorganic oxides (U.S. Pat. No. 4,956,518) and zeolites of ZSM-4, ZSM-18, ZSM-20 types, Beta zeolite (U.S. Pat. No 4,992,616; 4,384,161, PCT/U.S. Pat. No. 92/00,948) the alkylation of isobutane was catalyzed with butylenes.

The application of wide-pore zeolites in combination with Lewis acids enhanced, according to the patent, catalyst activity and alkylation selectivity. A disadvantage of catalysts of this type is employment of high-toxic and aggressive compounds as the active catalyst component.

The second approach resides in searching and synthesizing an active component of a new nature from a class of solid acids. First of all, it is necessary to intensify the acid properties of different zeolites by varying the cationic form and to use a dealuminizing process.

This approach is illustrated by wide-pore crystalline alumino-silicates—zeolites X, Y and cationic forms thereof, which are recommended as alkylation catalysts in U.S. Pat. No. 3,251,902, No. 3,549,557, No. 3,655,813, No. 3,893, 942, No. 4,992,615.

The third approach is based on the use of a polymeric matrix with grafted (immobilized) functional groups displaying strong acid properties.

Macroseticular organic ion-exchange resins in the cationic form are disclosed as alkylation catalysts in U.S. Pat. No. 3,862,258; No. 3,855,342.

The analysis set forth above deals with new processes of alkylation of isoparaffin hydrocarbons (isobutane above all) with olefins (butylenes) for producing a high-octane gasoline component (a mixture of isoparaffin hydrocarbons), for which purpose solid acid catalysts of a different nature are used.

However, these catalysts have low power expressed in an amount of alkylate obtained from one gram of catalyst in a run between two regenerations and also show low alkylate efficiency expressed in grams of alkylate per gram of catalyst for an hour. Most patents provide experimental data obtained in a periodic mode in an autoclave. For the reasons, scaled above, these said catalysts have not thus far found their practical application and have not been introduced on an industrial scale.

The closest reference to the invention is U.S. Pat. No. 4,992,616 from which known is a process for alkylating isoparaffins containing 4 to 22 carbon atoms with olefin containing 2 to 12 carbon atoms; characterized in that the catalyst employed is represented by wide-pore ZSM-3, ZSM-4, ZSM-12, ZSM-18, ZSM-20, zeolites modified with Lewis acids ($BF_3$, $AlCl_3$, $BCl_3$, $SbF_5$) in the presence of water or compounds containing it to improve process performance. As a result of use of a new catalyst the productivity of a reactor volume, the yield of the initial olefin and power are as follows:

2.0–2.1 $g/g_{catalyst} \times hr$

190–210% by weight

500–600 $g_{alkylate}/g$ catalyst

The claimed process is disadvantageous in that a catalyst containing high-toxic corrosion-active Lewis acids is used and that it cannot be regenerated.

Disclosed in Japanese Patent No. 61-242461 (A) is a catalyst for alkylating isoparaffins with olefins, which catalyst is obtained by introducing a sulphuric acid component and rare earth element compounds into the Group IV, metal oxide followed by activation through calcination at temperature comprised between 400 and 800° C. The alkylation process is conducted at temperatures from 0 to 200° C., a pressure between 1 and 60 atm., a feed stock containing isobutane and olefins with a molar ratio of 1 to 20, respectively. As a result of application of a new catalyst the productivity of a reactor volume, the initial olefin yield and the catalyst power are as follows:

0.2–0.3 $g/g_{catalyst} \times hr$

99–100% by weight

20–50 g $_{alkylate}/g$ catalyst

The deactivated catalyst may be subjected to oxidizing regeneration by calocination in the air at a temperature comprised between 400 and 500° C.

A disadvantage of the claimed catalyst is low power and a low alkylate yield per initial olefin.

DESCRIPTION OF THE INVENTION

It is the principal object of the present invention to provide an ecologically safe process for preparing high-octane gasoline components on a heterogeneous solid acid catalyst by alkylating isobutane with butylenes.

Said object is attained by charging into a reactor vessel a catalyst which comprises an active component in the form of a metal-complex or metaloxopolymeric compound of the general formula $H_k(Me^1)$; $(Me^2)_m O_n X_p$, wherein k=1–6; j=1–3; m=1–5; n=1–10, p=2–10, which is chemically fixed or applied to the surface of an inorganic matrix, wherein $Me^1$=a metal, Group IV; Ti, Zr, Hf, Sn; $Me^2$=a metal, Groups II–IV; X=$F^-$, $Cl^-$, $SO_4^{2-}$, $PO_4^{3-}$, $FSO_3^-$, $ClSO_3^-$, $FPO_3^{2-}$, $F_2PO_2^-$, or any combination thereof, the active component being dispersed on the surface of a porous matrix in the form of particles having a typical size of from about 10 to 500Å;

a matrix comprising a porous inorganic or organic material;

the Groups II–IV metal oxide;

the Group VIII metal such as Pt, Pd, Ru, Os, Ir.

The investigations of the inventors showed that isobutane alkylation with olefins proceeds most effectively on a catalyst comprising the metal-complex or metaloxopolymeric compound of the Group IV metal of said general formula, which catalyst is applied or chemically fixed on the surface of a porous inorganic or organic material, and along with this, the improved catalyst activity, as compared to the prior art catalyst activity is ensured by:

a) a stoichiometric composition of an active acid catalyst component that determines a narrow range of active acid centers which selectively catalyze precisely the isobutane alkylation reaction;

b) a high degree of dispersion of a metal-complex compound on the surface of a porous support, which leads to increasing the number of active centers participating in the reaction.

Various porous inorganic materials have been used for preparing a catalyst: high-silica zeolites, the oxides of the Groups II–IV elements or mixtures thereof, porous carbon materials and polymers porous organic.

Increased catalyst activity and improved selectivity are achieved by introducing the oxides of the Groups II–IV elements into the catalyst composition, this occurs due to the increased activity of the catalyst surface in a hydrogen disproportionation reaction promoting a fuller involvement of an isobutane component of the feedstock into the alkylation process.

An increased catalyst power and improved selectivity with respect to the most high-octane components of alkylate such as trimethylpentanes, is likewise attained by introducing the Group VIII elements into the catalyst composition and by conducting a process of alkylation in hydrogen or a hydrogen-containing gas. In this case there occurs hydrogenation of high-molecular olefin hydrocarbons which deactivate the active catalyst surface.

The highest catalyst activity, selectivity and power are achieved when the alkylation process is conducted at temperatures and pressures ensuring the supercritical state of the feed stock components in the reactor volume.

It has been found that the introduction into the feed stock for alkylation of hydrocarbons having from 5 to 10 carbon atoms in an amount of from 10 to 20% by weight increases the catalyst power. A high dissolving power of hydrocarbons results in removing, from the reactor volume, olefin polymerization products which deactivate the catalyst, thus making the run between two regenerations longer and the catalyst power greater.

The claimed composition relates to multiaction catalysts, i.e. it is capable of fully restoring its catalyst properties (activity, selectivity, power) after regeneration.

In the claimed alkylation process, a catalyst is regenerated by extracting the deactivating components from the catalyst surface using a solvent at elevated temperatures and pressures. To wash the catalyst bed, use can be made of single-component or complex solvents belonging to different classes of organic substances.

Such solvents include:

aromatic hydrocarbons: benzene, toluene, xylenes, etc.;

oxygen-containing organic compounds—ether, dioxane, methyl-ethyl ketone, etc.;

halogen-containing organic compounds: carbon tetrachloride, dichloromethane, dichloroethane, etc.;

inorganic solvents: carbon dioxide, sulfur dioxide.

The solvent is fed into a reactor space at a temperature comprised between 50 and 200° C. and a pressure that allows for the solvent to be present in the reactor in the liquid state.

A regeneration process results, in such conditions, in extracting resinous products from the active catalyst centers and in regenerating catalyst activity, selectivity and power similar to those of a fresh catalyst.

The regeneration of catalyst activity, using the devised method does not change, as distinct from traditional oxidizing regeneration at high temperatures, the morphological and structural characteristics of catalyst grain (surface, porosity), a factor that increases the catalyst service life by many times.

The increase or decrease of the content of the corresponding components outside the said range results in reducing the target product yield due to a lower conversion of butylenes and a lower yield of alkylate per the initial butylene, and also to a lower catalyst power.

Preferred embodiment of the invention

The process for preparing high-octane gasoline components of an isoparaffin nature is carried out in using, as the feed stock components, isobutane and butylenes of different isomeric compositions, or hydrocarbon fractions comtaining isobutane and butylenes. In the examples as given below catalyst activity, selectivity, productivity and power have been obtained in using, as the alkylation feedstock industrial hydrocarbon fractions (wt. %):

| Isobutane fraction | | Butylene fraction | |
|---|---|---|---|
| C2 | 0.1 | C2 | 0.1 |
| C3 | 1.5 | C3 | 7.8 |
| butane | 3.9 | butane | 17.0 |
| isobutane | 93.2 | isobutane | 37.7 |
| butylenes | 1.2 | butylenes | 34.1 |
| C5+ hydrocarbons | 0.4 | C5+ hydrocarbons | 3.3 |

An alkylation catalyst is prepared in the following manner: first synthesized is a metal-complex compound. A porous support is impregnated with an aqueous solution of said metal-complex compound and dried at a temperature comprised between 100 and 200° C. An active catalyst component is finally formed by calcination at a temperature of from about 400 to about 600° C. in atmospheric air or inert gas.

To grasp a better idea of the concept of the present invention, concrete examples are given below.

EXAMPLE 1

20 g of a silica gel are mixed with 20 ml of an aqueous solution containing 2.34 g of zirconyl nitrate and 0.043 g Pt in the form of chloroplatinic acid. Dried at 110° C. for 10 hours, thereafter calcined at 550° C. for 3 hours to give an alkylation catalyst support.

In 100 ml of an aqueous solution containing 50 g of zirconylsulfuric acid are dissolved in 8.81 g of zinc chloride, with a metal-complex compound forming in the solution. The compound has the formula $HZnZrO(SO_4)_2$. The resulting solution is maintained on a water bath, at 95° C. for 5 hours.

Into the resulting solution is introduced a support for an alkylation catalyst, maintained for 3 hours, dried at 150° C. for 10 hours and calcined at 550° C. for 3 hours. The alkylation catalyst obtained is of the following chemical composition: $ZrO_2$—5.4% by weight, $HZnZrO(SO_4)_2$—12.2% by weight, $SiO_2$—81.0% by weight, Pt—0.2% by weight.

A flow-through tubular reaction vessel is charged with a catalyst (10 g). The reaction vessel is preheated up to 75° C., blown out with helium, followed by an isobutane fraction passed at a rate of 3 $g/g_{catalyst}$ hr for 1 hour. After isobutane blowing, the feedstock is fed, the latter is prepared by mixing 0.37 kg of a butylene fraction and 1.00 kg of said isobutane fraction at a rate of 6.4 $g/ml_{cat}$x hr. The molar ratio of isobutane to butylenes in the feed stock is 10.3. The pressure in the reaction vessel is 17 atm. Reaction products are admitted to a separator through a pressure regulator, said separator being colled to 0° C. Gaseous and liquid products are assayed separately, using a chromatographic analysis. The process is conducted for 400 hours.

On the basis of chromatographic analysis data is calculated:

productivity of the reactor volume $P=M_a/V_{cat}$, wherein $M_a$=the quantity of liquid alkylate in g, which is formed in a one hour reaction, $V_{cat}$=the catalyst volume, ml;

conversion of butylenes (%) according to the formula: $X=100^x (C_n-C_k)/C_n$, wherein $C_n$=the concentration of butylenes at the reactor inlet mol %, $C_k$=the concentration of butylenes at the reactor outlet mol %;

the yield of alkylate per initial olefin: $A=P/(W^x C_n^y)$, wherein P=the productivity of the reactor volume, W=the feed stock feed rate, expressed in $g/ml_{cat}$x hr, $C_n^y$=the concentration of butylenes in the feed stock, % by weight;

the content of trimethylpentanes in the alkylate: $TMP=M_{tmp}/M_{alkylate} \times 100$, wherein $M_{tmp}$=the amount of trimethylpentanes in the alkylate in g, $M_{alkylate}$=the amount of the alkylate resulting from the reaction, in g; TMP=the concentration of trimethylpentanes in the alkylate, % by weight;

the catalyst power $R=P^x T$, wherein R=the productivity of the reactor volume, T=the time during which olefin conversion is reduced by 10%.

The Process results:

the alkylate efficiency, E=0.93 $g/ml_{cat}$ per hr the average butylene conversion (for 400 hours), X=97% the liquid alkylate yield per initial butylenes A=202% the catalyst power, P=195 $g/ml_{cat}$.

EXAMPLE 2

Alkylate is prepared in the same manner as in Example 1, with the exception that the isobutane/butylene feed stock is saturated with hydrogen under the pressure of 25 atm. The catalyst characteristics, the conditions and the process results are given in Table 1.

EXAMPLES 3–11

Alkylate is prepared in the same manner as in Example 1, with the exception that in addition to temperature, the feed stock rate, the pressure and the molar ratio of isobutane/butylenes are varied. The catalyst characteristics, the conditions and the process results are given in Table 1.

EXAMPLES 12–22

Alkylate is prepared in the same manner as in Example 1, with the exception that composition and the quantity of a metal-complex compound applied to the surface of a silica gel are varied. The catalyst characteristics and the process conditions are given in Table 2 and in Figures.

EXAMPLES 23–32

Alkylate is prepared in the same manner as in Example 1, with the exception that varied is the chemical nature of a porous support is varied. The characteristics and the process results are given in Table 3.

EXAMPLES 33–34

Alkylate is prepared in the same manner as in Example 1, with the exception that the degree of dispersion of an active component in the catalyst is varied. The catalyst characteristics and the process results are given in Table 4 and in FIGS. 1, 2.

EXAMPLE 35

Alkylate is prepared in the same manner as in Example 1, with the exception that the feed stock is added with an alkylate in an amount of 15.2% by weight. The process performance is as follows:

the alkylate efficiency, $E=0.95$ g/ml$_{cat}$ x hr the average butylenes conversion (for 13 5 hrs), $X=97\%$ the liquid alkylate yield per initial butylene $A=205\%$ the catalyst power, $R=249$ g/ml$_{cat}$.

the content of trimethylpentanes, $TMP=76.3\%$

EXAMPLE 36

The deactivated catalyst of Example 1 is treated in a tubular reactor in a toluene flow, 5 g/g$_{cat}$.x hr at 170° C., pressure 15 atm., for 5 hours. The regenerated catalyst has the following characteristics:

the alkylate efficiency, $E=0.95$ g/ml$_{cat}$ x hr the average butylenes conversion (for 400 hrs), $X=98\%$ the liquid alkylate yield per initial butylenes, $A=200\%$ the catalyst power, $P=195$ g/ml$_{cat}$.

EXAMPLE 37

The deactivated catalyst of Example 1 is treated in a tubular reactor in an ether flow, 3 g/g$_{cat}$. x hr, at 90° C., the pressure 29 atm. for 5 hours. The regenerated catalyst has the following characteristics:

the alkylate productivity, $P=0.85$ g/ml$_{cat}$ . x hr the average butylenes conversion (for 400 hours), $X=96\%$ liquid alkylate yield per initial butylenes $A=180\%$ the catalyst power, $R=174$ g/ml$_{cat}$.

EXAMPLE 38

The deactivated catalyst of Example 1 is treated in a tubular reaction vessel in a dichloroethane flow, 7 g/g$_{cat}$. x hr, at 110° C. a pressure 35 atm., for 5 hours. The regenerated catalyst has the following characteristics:

the alkylate efficiency, $E=0.99$ g/ml$_{cat}$. x hr.

the average butylenes conversion (for 400 hours), $X=98\%$ the yield of liquid alkylate yield per initial butylenes, $A=195\%$ the catalyst power, $R=192$ g/ml$_{cat}$.

EXAMPLE 39

The deactivated catalyst of Example 1 is treated in a tubular reaction vessel in a carbon dioxide flow, 9 g/g$_{cat}$. x hr, at 60° C., a pressure 90 atm, for 5 hours. The regenerated catalyst has the following characteristics:

the alkylate efficiency, $E=0.97$ g/ml$_{cat}$ x hr.

butylenes conversion (for 400 hours), $X=98\%$ the liquid alkylate, yield per initial butylenes $A=204\%$ the catalyst power, $p=197$ g/ml$_{cat}$.

Industrial applicability

The claimed process may find a variety of applications in the industry to obtain ecologically pure fuels. It can be utilized in various branches of the chemical industry, including the oil refining industry.

TABLE 1

The influence of temperature, pressure, phase state and feed stock rate, isobutane/butylenes molar ratio on the alkylation process performance. The alkylation catalyst comprises: $ZrO_2$-5.4, % by weight, $HZnZrO(SO_4)_2$-12.2, % by weight, $SiO_2$-81.0, % by weight, Pt-0.2, % by weight

| N | T, °C. | P, atm | feed stock crit. param. | Phase state | feed stock feed rate, g/ml.hr | Iso-butylen, mol | P, g/ml.hr | X, % | A, % | Power g/ml, R | TMP % by weight |
|---|---|---|---|---|---|---|---|---|---|---|---|
| 1 | 75 | 17 | $T_{cr}$ = 136° C. $P_{cr}$ = 36 atm. | liquid | 6.4 | 10.3 | 0.93 | 97 | 202 | 195 | 72.3 |
| 2 | 75 | 17 | $T_{cr}$ = 136° C. $P_{cr}$ = 36 atm | liquid | 6.4 | 10.3 | 0.93 | 97 | 202 | 390 | 72.3 |
| 3 | 160 | 39 | $T_{cr}$ = 136° C. $P_{cr}$ = 36 atm | super-critical | 6.3 | 10.3 | 0.99 | 99 | 201 | 198 | 72.0 |
| 4 | 160 | 39 | $T_{cr}$ = 136° C. $P_{cr}$ = 36 atm | super-critical | 5.1 | 5.8 | 0.94 | 95 | 169 | 169 | 71.4 |
| 5 | 160 | 12 | $T_{cr}$ = 136° C. $P_{cr}$ = 36 atm | gas | 6.3 | 12.9 | 0.71 | 99 | 203 | 105 | 54.2 |
| 6 | 135 | 32 | $T_{cr}$ = 136° C. $P_{cr}$ = 36 atm | critical | 8.1 | 12.9 | 0.90 | 99 | 199 | 195 | 59.8 |
| 7 | 100 | 15 | Tcr = 136° C. Pcr = 36 atm | gas liquid | 5.1 | 12.9 | 0.53 | 95 | 186 | not found | 56.1 |
| 8 | 100 | 8 | Tcr = 136° C. Pcr = 36 atm | gas | 1.9 | 15.6 | 0.13 | 96 | 184 | not found | 42.4 |
| 9 | 100 | 8 | Tcr = 136° C. Pcr = 36 atm | gas | 1.9 | 5 | 0.15 | 93 | 165 | 159 | 37.2 |
| 10 | 80 | 8 | Tcr = 136° C. Pcr = 36 atm | gas | 1.0 | 12 | 0.07 | 86 | 132 | not found | 39.9 |
| 11 | 50 | I | Tcr = 136° C. Pcr = 36 atm | gas | 1.0 | 12 | 0.08 | 69 | 144 | 100 | 48.4 |

TABLE 2

The influence of the composition and quantity of a metal-complex compound applied to a silica gel. Alkylation temperature 75° C., pressure 17 atm., feed stock feed rate speed 1.0 g/ml$_{cat}$ × hr. Isobutane/butylenes molar ratio = 5.8, feed stock feed rate - 4.2 g/g$_{cat}$ × hr

| N | Catalyst, chem. composition, % by weight | P g/ml | X hr | A % | Power g/ml | TMP % by weight |
|---|---|---|---|---|---|---|
| 12 | 0.6 TiO$_2$, 7.2 HZnTiO(SO$_4$)$_2$, 92.2 SiO$_2$ | 0.25 | 98 | 195 | 167 | 70.3 |
| 13 | 1.8 TiO$_2$, 12.2 Zn$_2$ TiO(SO$_4$)$_2$, 86 SiO$_2$ | 0.24 | 99 | 186 | 169 | 71.0 |
| 14 | 0.9 TiO$_2$, 11.8 H$_2$Al$_2$TiO(SO$_4$)$_2$, 0.5 Pt, 86.8 SiO$_2$ | 0.21 | 94 | 199 | 184 | 73.4 |
| 15 | 10.2 H$_2$TiF$_6$, 5.0 SnO$_2$ 84.4 SiO$_2$ | 0.16 | 91 | 146 | 111 | 54.2 |
| 16 | 1.8 TiO$_2$, 13.0 H$_3$Al$_3$Ti$_5$T$_{12}$, 0.2 Pt, 85.0 SiO$_2$ | 0.18 | 95 | 151 | 153 | 59.8 |
| 17 | 1.8 TiO$_2$, 10.2 HZnTiOF$_4$, 88 SiO$_2$ | 0.18 | 84 | 142 | not found | 56.1 |
| 18 | 0.5 ZrO$_2$, 10.5 H$_2$ZrO(SO$_4$)$_2$, 0.5 Pt 88.5 SiO$_2$ | 0.27 | 99 | 210 | 169 | 42.4 |
| 19 | 15.5 HZnZrO(SO$_4$)$_2$, 20.6 ZhO 63.9 SiO$_2$ | 0.23 | 97 | 183 | 174 | 49.1 |
| 20 | 2.0 ZrO$_2$, 11.5 H$_6$Al$_3$Zr$_2$O$_2$(SO$_4$)$_2$, 0.1 Pt 86.4 SiO$_2$ | 0.15 | 81 | 119 | not found | 39.9 |
| 21 | 2.0 ZrO$_2$, 7.2 H$_2$ZrO(ClSO$_4$)$_2$, 90.8 SiO$_2$ | 0.26 | 99 | 210 | 95 | 48.3 |
| 22 | 12.0 ZrO$_2$, 27.0 H$_2$AlZrO (FSO$_3$)$_2$, 0.01 Pd 60.99 SiO$_2$ | 0.26 | 99 | 210 | 118 | 59.9 |

TABLE 3

The influence of the nature of a porous alkylation catalyst support on the alkylation process performance. Alkylation temperature 100° C., pressure 8 atm, feed stock rate 4.3 g/ml$_{cat.}$ × hr. Isobutane/butylenes molar ratio = 8. The catalyst composition: ZrO$_2$-0.8% by weight; HAIZrO (SO$_4$)$_2$, 12.2 % by weight, porous support 87.0%.

| No | Porous support | P, g/ml × hr | X, % | A, % | R, g/ml |
|---|---|---|---|---|---|
| 23 | Gamma-Alumina | 0.25 | 86 | 93 | 250 |
| 24 | Carbon support "Subunit" | 0.55 | 97 | 189 | 192 |
| 25 | Amorphous aluminosilicate | 0.54 | 92 | 195 | 180 |
| 26 | Copolymer of styrene and divinylbenzene | 0.57 | 95 | 199 | 190 |
| 27 | Zeoline ZSM-5, agglomerated crystals of foliaceous morphology, typical size 0.1 mcm, 94.5 SiO$_2$, 3.53 Al$_2$O$_3$, 0.6 Fe$_2$O$_3$, 0.39 Na$_2$O | 0.23 | 97 | 183 | 174 |
| 28 | Zeolite ZSM-5, agglomerated crystals of foliaceous morphology, typical size 0.7 mcm, 94.5 SiO$_2$, 2.4 Al$_2$O$_3$, 0.9 Fe$_2$O$_3$, 0.01 Na$_2$O | 0.23 | 98 | 185 | 153 |
| 29 | Zeolite ZSM-5, crystals of hexagonal morphology, typical size 3–4 mcm, 97.3 SiO$_2$, 1.6 Al$_2$O$_3$, 0.9 Fe$_2$O$_3$, 0.04 Na$_2$O | 0.12 | 71 | 103 | not found |
| 30 | Zeolite ZSM-12, agglomerated crystals of hexagonal morphology, typical size 98.5 SiO$_2$, 1.4 Al$_2$O$_3$, 0.09 Fe$_2$O$_3$, 0.01 Na$_2$O | 0.21 | 95 | 174 | 109 |
| 31 | Zeolite Beta, agglomerated crystals, typical size 0.7 mcm 95.8 SiO$_2$, 3.3 Al$_2$O$_3$, 0.03 Fe$_2$O$_3$, 0.03 Na$_2$O | 0.25 | 98 | 203 | 153 |
| 32 | Zeolite Beta, agglomerated crystals, typical size 0.5 mcm, 92.7 SiO$_2$, 7.1 Al$_2$O$_3$, 0.03 Fe$_2$O$_3$, 0.08 Na$_2$O | 0.24 | 98 | 192 | 120 |

TABLE 4

The influence of the degree of dispersion of an alkylation catalyst active component on the alkylation process performance. Alkylation temperature 100° C., pressure 23 atm, feed stock feed rate 4.3 g/ml$_{cat}$ × hr. Isobutane/butylenes molar ratio = 8. Catalyst composition: ZrO$_2$-0.8 % by weight, HAIZrO (SO$_4$)$_2$, 11–12 % by weight, porous support 87.0%

| No | Porous support | Active comp. dispersion, A | P, g/ml.hr | X, % | A, % | R, g/ml |
|---|---|---|---|---|---|---|
| 33 | Silica gel | 30–50 (FIG. 1) | 0.55 | 94 | 183 | 251 |
| 34 | Carbon support "Subunit" | 30–100 (FIG. 2) | 0.57 | 97 | 189 | 280 |

We claim:

1. A process for preparing high-octane gasoline components comprising contacting feed stock components including isobutane and olefins with a solid heterogeneous acid catalyst at a temperature from about 50–160° C. and a pressure from about 1 to 40 atm, and maintaining an isobutane/olefins ratio in the zone of alkylation at about 1–40, said solid heterogeneous acid catalyst comprising a metal-complex or metaloxopolymeric compound of the general formula H$_k$(Me$^1$)$_j$(Me$^2$)$_m$O$_n$X$_p$, wherein Me$^1$ is a Group IV metal, Me$^2$ is a Group II or III metal, X is a mono- or polyvalent anion, k=1–6, j=1–3, m=1–5, n=1–10, and p=2–10, dispersed on the surface of a porous matrix in the form of particles having a size of from about 10–500Å.

2. A process according to claim 1, wherein the contacting occurs in a reactor and wherein the temperature and pressure are selected such that the feed stock components are in a supercritical state in the reactor.

3. A process according to claim 1, wherein the contacting occurs in a reactor and the feed stock components are introduced into the reactor in a liquid state.

4. A process according to claim 3, wherein the feed stock components include a hydrocarbon having from 5 to 10 carbon atoms in an amount between 1 and 20% by weight.

5. A process according to claim 3, wherein the feed stock components are introduced into the reactor with hydrogen or a hydrogen-containing gas in an amount between 0.5 and 5% by weight.

6. A process according to claim 1, wherein said feed stock components consist essentially of isobutanes and butylenes.

7. A process according to claim 1, further comprising regenerating the catalyst with a solvent or a mixture of solvents comprising compounds selected from the group consisting of aromatic hydrocarbons, isoparaffins, oxygen-containing organic compounds, halogen-containing organic compounds, inorganic solvents and mixtures thereof at a temperature between 50 and 200° C. and at a pressure of from about 1 to about 100 atm.

8. A catalyst for preparing high-octane gasoline components comprising a porous matrix and a metal-complex or metaloxopolymeric compound of the general formula $H_k(Me^1)_j(Me^2)_m O_n X_p$, wherein $Me^1$ is a Group IV metal, $Me^2$ is a Group II or III metal, X is a mono- or polyvalent anion, k=1–6, j=1–3, m=1–5, n=1–10, and p=2–10, dispersed on the surface of the porous matrix in the form of particles having a size of from about 10–500Å.

9. A catalyst according to claim 8, wherein $Me^1$ is a Group IV metal selected from the group consisting of Ti, Zr and Hf.

10. A catalyst according to claim 8, wherein $Me^2$ is a Group II or III metal selected from the group consisting of Zn, Cd and Al.

11. A catalyst according to claim 8, wherein X is an anion selected from the group consisting of $F^-$, $Cl^-$, $SO_4^{2-}$, $PO_4^{3-}$, $FSO^-_3$, $ClSO^-_3$, $FPO^{2-}_3$, $F_2PO_2^-$ and mixtures thereof.

12. A catalyst according to claim 8, wherein the metal-complex or metaloxopolymeric compound is present in the catalyst in an amount of between 3 and 50 by weight.

13. A catalyst according to claim 8, wherein the catalyst further comprises a Group VIII metal in an amount between 0.01 and 1.0% by weight.

14. A catalyst according to claim 8, wherein the catalyst further comprises an oxide of a Group II, III or IV metal in an amount of between 0.1 and 20.0% by weight.

15. A catalyst according to claim 8, wherein the matrix comprises an inorganic porous material.

16. A catalyst according to claim 8, wherein the matrix comprises a porous carbon material.

17. A catalyst according to claim 8, wherein the matrix comprises a porous organic material.

\* \* \* \* \*